United States Patent
Aoki

(10) Patent No.: US 9,895,136 B2
(45) Date of Patent: Feb. 20, 2018

(54) ULTRASOUND DIAGNOSIS APPARATUS WITH A PROBE AND A GROUNDING SWITCH FEATURE

(71) Applicant: Toshiba Medical Systems Corporation, Otawara-shi (JP)

(72) Inventor: Minoru Aoki, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 659 days.

(21) Appl. No.: 13/859,352

(22) Filed: Apr. 9, 2013

(65) Prior Publication Data
US 2013/0231568 A1  Sep. 5, 2013

Related U.S. Application Data

(63) Continuation of application No. PCT/JP2011/073952, filed on Oct. 18, 2011.

(30) Foreign Application Priority Data

Oct. 20, 2010  (JP) ................................ 2010-235809

(51) Int. Cl.
- *A61B 8/00* (2006.01)
- *B06B 1/06* (2006.01)
- *G01S 7/52* (2006.01)

(52) U.S. Cl.
CPC .............. *A61B 8/4444* (2013.01); *B06B 1/06* (2013.01); *A61B 8/4433* (2013.01); *G01S 7/5208* (2013.01)

(58) Field of Classification Search
CPC ................................ A61B 8/4444; B06B 1/06
See application file for complete search history.

(56) References Cited

U.S. PATENT DOCUMENTS

| 5,327,895 A | 7/1994 | Hashimoto et al. |
| 5,671,746 A * | 9/1997 | Dreschel ............... B06B 1/0633 600/459 |
| 2004/0073118 A1 | 4/2004 | Peszynski et al. |
| 2004/0260181 A1 | 12/2004 | Makita et al. |
| 2005/0225916 A1 | 10/2005 | Bolorforosh et al. |
| 2010/0059344 A1* | 3/2010 | Belanger et al. ............ 200/61.2 |

FOREIGN PATENT DOCUMENTS

| JP | 04-097743 | 3/1992 |
| JP | 07-038998 | 2/1995 |
| JP | 10-094540 | 4/1998 |

(Continued)

OTHER PUBLICATIONS

English translation of JP2000217196.*

(Continued)

*Primary Examiner* — Serkan Akar

(74) *Attorney, Agent, or Firm* — Oblon, McClelland, Maier & Neustadt, L.L.P.

(57) ABSTRACT

According to the present embodiment, the ultrasound probe includes a piezoelectric vibrator, an open/short switching board, a short terminal, and a GND terminal. Then, the open/short switching board and the short terminal switch between a short state in which the electrode of the piezoelectric vibrator is connected to the GND terminal and an open state in which the electrode of the piezoelectric vibrator is not connected to the GND terminal, at any timing.

8 Claims, 7 Drawing Sheets

(56) References Cited

FOREIGN PATENT DOCUMENTS

| JP | 10-104387 A    | 4/1998 |
|----|----------------|--------|
| JP | 2000-217196    | 8/2000 |
| JP | 2003-230194 A  | 8/2003 |
| JP | 2004-130137    | 4/2004 |
| JP | 2004-230033    | 8/2004 |
| JP | 2010-110366 A  | 5/2010 |

OTHER PUBLICATIONS

International Search Report dated Nov. 22, 2011 for PCT/JP2011/073952 filed Oct. 18, 2011 with English Translation.
International Written Opinion dated Nov. 22, 2011 for PCT/JP2011/073952 filed in Oct. 18, 2011.
Office Action dated Sep. 2, 2014 in Japanese Patent Application No. 2010-235809 (with English language translation).
Extended European Search Report dated Dec. 8, 2016 in Patent Application No. 11834358.1.

* cited by examiner

FIG.3

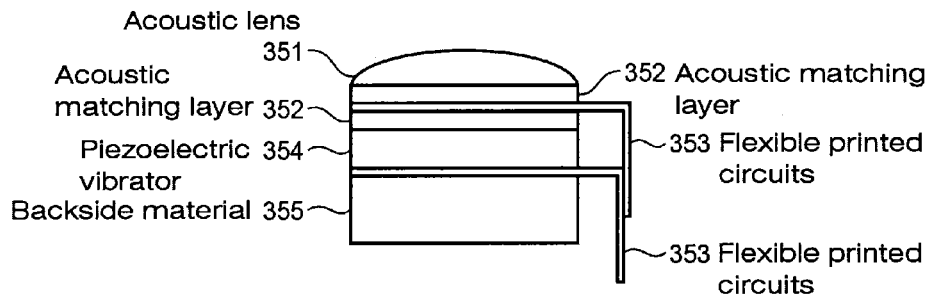

- Acoustic lens 351
- Acoustic matching layer 352
- 352 Acoustic matching layer
- Piezoelectric vibrator 354
- 353 Flexible printed circuits
- Backside material 355
- 353 Flexible printed circuits

FIG.4

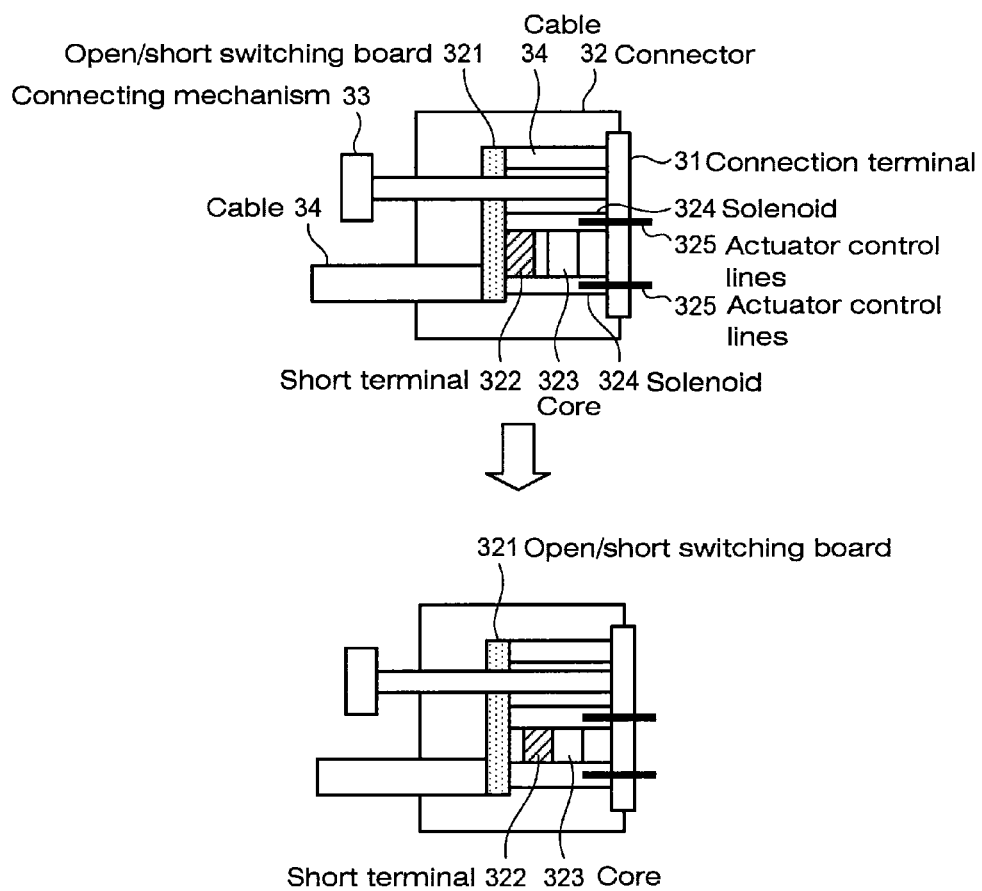

- Open/short switching board 321
- Cable 34
- 32 Connector
- Connecting mechanism 33
- 31 Connection terminal
- Cable 34
- 324 Solenoid
- 325 Actuator control lines
- 325 Actuator control lines
- Short terminal 322
- 323 Core
- 324 Solenoid

- 321 Open/short switching board
- Short terminal 322
- 323 Core

FIG.8
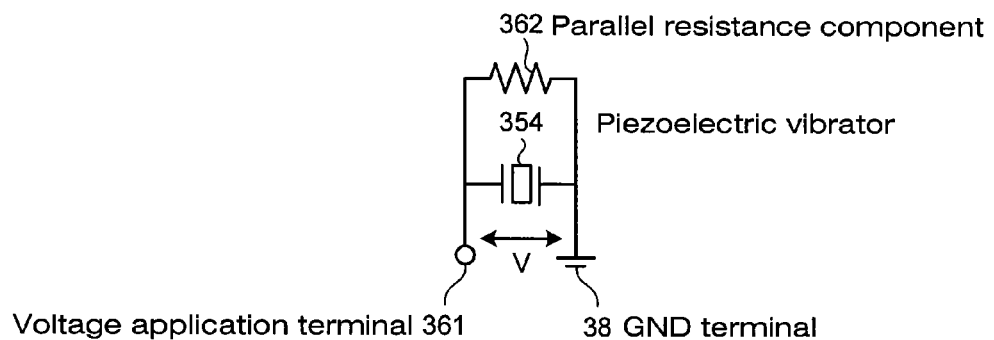
FIG.9
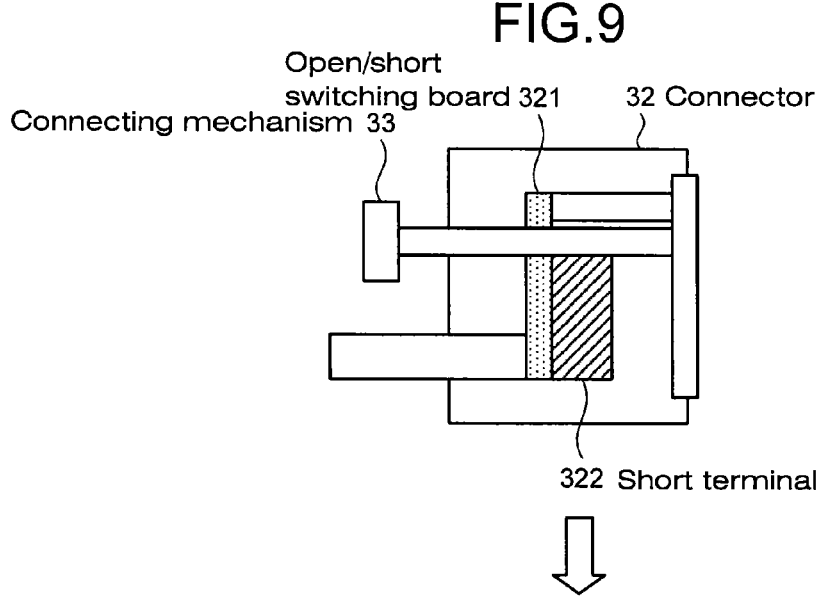
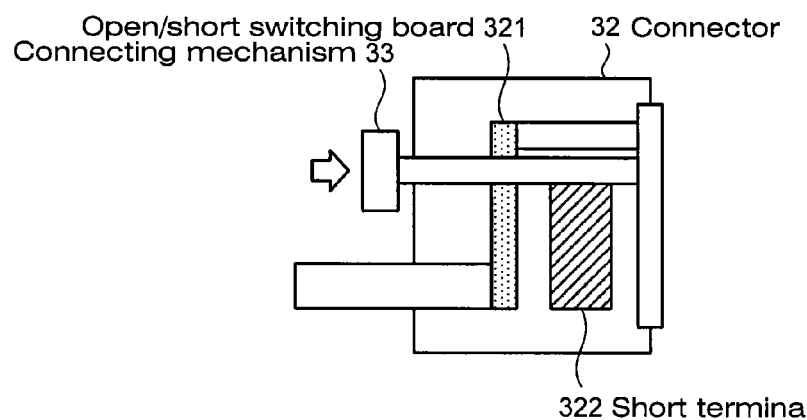

ULTRASOUND DIAGNOSIS APPARATUS WITH A PROBE AND A GROUNDING SWITCH FEATURE

CROSS-REFERENCE TO RELATED APPLICATIONS

This application is a continuation of PCT international application Ser. No. PCT/JP2011/073952 filed on Oct. 18, 2011 which designates the United States, and which claims the benefit of priority from Japanese Patent Application No. 2010-235809, filed on Oct. 20, 2010; the entire contents of which are incorporated herein by reference.

FIELD

Embodiments described herein relate generally to an ultrasound probe and an ultrasound diagnosis apparatus.

BACKGROUND

Conventionally, an ultrasound diagnosis apparatus is on a smaller scale than other medical image diagnosis apparatuses such as an X-ray diagnosis apparatus, an X-ray computed tomography (CT) apparatus, and a magnetic resonance imaging (MRI) apparatus. In addition, because it is an apparatus that can display in real time the movement of an examination target such as cardiac pulsation and fetal activity by a simple operation of placing an ultrasound probe on the surface of the body, the ultrasonic diagnosis apparatus plays an important role in the present medical practice. Moreover, ultrasound diagnosis apparatuses that are secure from radiation exposure include downsized ones so that they can be carried with one hand. Such ultrasound diagnosis apparatuses can be readily used in medical settings such as obstetrics and home healthcare.

The ultrasound diagnosis apparatus emits ultrasound waves from its ultrasound probe into the patient's body. Then, the ultrasound diagnosis apparatus receives, with the ultrasound probe, reflection waves caused by acoustic impedance mismatching inside the body of the patient, and generates a reception signal. The ultrasound probe is provided with multiple piezoelectric vibrators in the scanning direction to transmit and receive such ultrasound waves. These piezoelectric vibrators are piezoelectrically polarized in the directions of the ultrasound wave transmission and reception, generating ultrasound waves based on a transmission signal and generating a reception signal upon receiving reflection waves.

With the conventional technology, however, depolarization caused in the piezoelectric vibrators tend to lower the performance of the ultrasound probe.

BRIEF DESCRIPTION OF THE DRAWINGS

FIG. 3 is a diagram for explaining an ultrasound transmitting and receiving unit.

FIG. 4 is a diagram for explaining the structure of a connector of the ultrasound diagnosis apparatus according to the first embodiment.

FIG. 8 is a diagram for explaining a conventional example of an electric circuit regarding an electrode of a piezoelectric vibrator.

FIG. 9 is a diagram for explaining the structure of a connector of an ultrasound diagnosis apparatus according to the second embodiment.

DETAILED DESCRIPTION

In general, according to one embodiment, an ultrasound probe includes a piezoelectric vibrator and a switching unit. A piezoelectric vibrator configured to generate ultrasound waves. A switching unit configured to switch at any timing between a short state in which an electrode of the piezoelectric vibrator is connected to a ground unit and an open state in which the electrode of the piezoelectric vibrator is not connected to the ground unit.

Hereinafter, embodiments will be described with reference to the drawings.

[First Embodiment]

Figure 1:
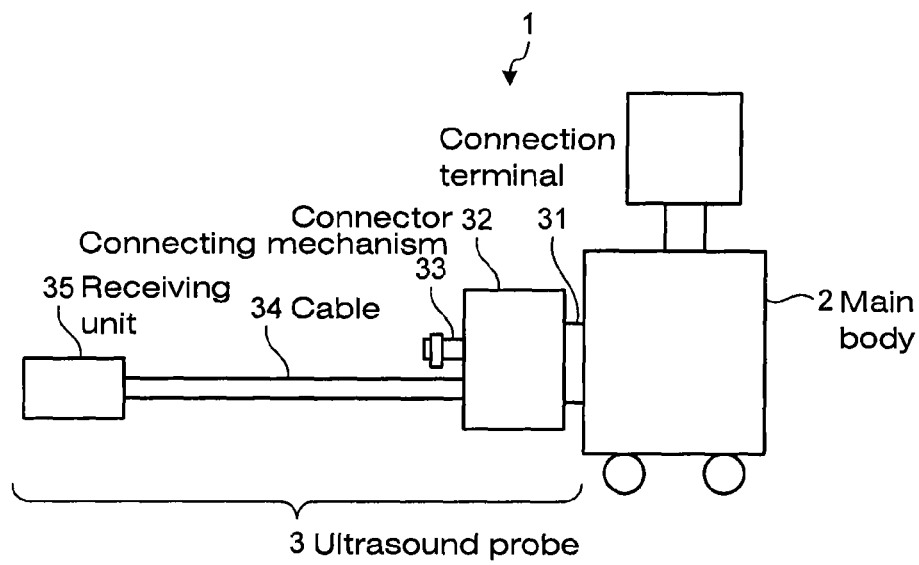
FIG. 1 is a diagram for explaining the entire structure of an ultrasound diagnosis apparatus according to the first embodiment.

First, the entire structure of the ultrasound diagnosis apparatus according to the first embodiment is explained with reference to FIG. 1. FIG. 1 is a diagram for explaining the entire structure of an ultrasound diagnosis apparatus 1 according to the first embodiment. As illustrated in FIG. 1, the ultrasound diagnosis apparatus 1 according to the first embodiment includes an apparatus main body 2 and an ultrasound probe 3.

The apparatus main body 2 is an apparatus that supplies a transmission signal so that the ultrasound probe 3 can transmit ultrasonic waves, and also creates an ultrasonic image based on the received reflection waves. The apparatus main body 2 is connected to an input device, a monitor, and the like so that it can receive various commands from the operator of the ultrasound diagnosis apparatus 1 and display various types of information.

The input device includes, for example, a trackball, switches, buttons, a mouse, and a keyboard, and it receives various setting requests from the operator of the ultrasound diagnosis apparatus 1, and transfers the various setting requests to the apparatus main body 2 (setting requests regarding the region of interest and image quality condition setting commands, for example).

The monitor is used to display a Graphical User Interface (GUI) for the operator of the ultrasound diagnosis apparatus 1 to input various setting requests by use of the input device and also to display ultrasonic images generated by the apparatus main body 2.

The ultrasound probe 3 includes a connection terminal 31, a connector 32, a connecting mechanism 33, a cable 34, and an ultrasound transmitting and receiving unit 35, as illustrated in FIG. 1. The connection terminal 31 is a terminal that connects the apparatus main body 2 and signal lines for transmitting transmission signals to the later-described ultrasound transmitting and receiving unit 35 and receiving reception signals from the ultrasound transmitting and receiving unit 35. The connection terminal 31 has different shapes to correspond to different types of the apparatus main bodies 2.

The connector 32 houses the cable 34 and fixes the ultrasound probe 3 to the apparatus main body 2 to ensure electric connections. The connecting mechanism 33 establishes the electric connections between the ultrasound probe 3 and the apparatus main body 2 by fixing the connector 32 to the apparatus main body 2. The connecting mechanism 33 may be a handle or a knob. Then, the connecting mechanism 33 switches between a lock state in which the connector 32 is fixed to the apparatus main body 2 and an unlock state in which the connector 32 can be detached from the apparatus main body 2.

Figure 2:
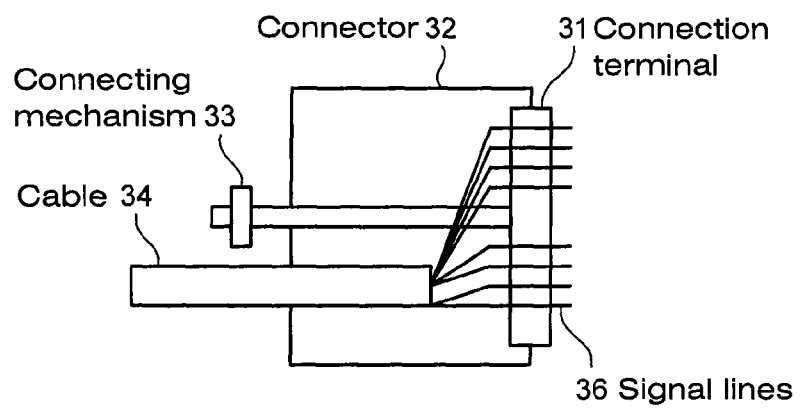
FIG. 2 is a diagram for explaining cables.

The cable 34 is a cable for transmitting and receiving signals between the later described ultrasound transmitting and receiving unit 35 and the apparatus main body 2. FIG. 2 is a diagram for explaining the cable 34. As illustrated in FIG. 2, the cable 34 includes several signal lines 36. Then, as illustrated in FIG. 2, the signal lines 36 are connected to the apparatus main body 2 by way of the connection terminal 31. The number of signal lines 36 corresponds to the number of piezoelectric vibrators included in the later described ultrasound transmitting and receiving unit 35.

The ultrasound transmitting and receiving unit 35 generates ultrasound waves in accordance with the transmission signal supplied by the apparatus main body 2, and furthermore, it receives reflection waves from the patient and converts them to a reception signal. FIG. 3 is a diagram for explaining the ultrasound transmitting and receiving unit 35.

As illustrated in FIG. 3, the ultrasound transmitting and receiving unit 35 includes an acoustic lens 351, an acoustic matching layer 352, flexible printed circuits (FPC) 353, a piezoelectric vibrator 354, and a backside material (backing material) 355.

The acoustic lens 351 brings the ultrasound waves into convergence. The acoustic matching layer 352 reduces the mismatching of the acoustic impedances of the piezoelectric vibrator 354 and the patient. The FPC 353 transmits and receives electric signals to and from the piezoelectric vibrator 354. The FPC 353 is connected to the signal lines 36, although it is not shown.

The piezoelectric vibrator 354 generates ultrasound waves in accordance with the transmission signal supplied from the apparatus main body 2, receives reflection waves from the patient, and generates a reception signal. The piezoelectric vibrator 354 includes multiple piezoelectric vibrators, although they are not shown, and each of the piezoelectric vibrators generates ultrasound waves and generates a reception signal. The backside material 355 prevents the ultrasound waves from propagating from the piezoelectric vibrator 354 backward.

For example, when the ultrasound transmitting and receiving unit 35 transmits ultrasound waves to the patient, the transmitted ultrasound waves are successively reflected on the body tissue of the patient where the acoustic impedances are discontinuous, and received by the multiple piezoelectric vibrators of the ultrasound transmitting and receiving unit 35 as reflection wave signals. The amplitude of a received reflection wave signal depends on the difference between the acoustic impedances of the discontinuous surfaces on which the ultrasound waves are reflected. If the transmitted ultrasonic pulse is reflected in the flowing blood current or on the surface of the cardiac wall, the reflection signals have their frequencies shifted due to the Doppler effect, in accordance with the velocity component of the moving body with respect to the direction of the ultrasound wave transmission.

According to the present embodiment, a one-dimensional ultrasound probe in which multiple piezoelectric vibrators are arranged in a line may be adopted for the ultrasound probe 3, or an ultrasound probe 3 that mechanically shakes the multiple piezoelectric vibrators of the one-dimensional ultrasound probe or a two-dimensional ultrasound probe in which multiple piezoelectric vibrators are two-dimensionally arranged in a matrix form may be adopted.

In this manner, the ultrasound diagnosis apparatus 1 according to the first embodiment creates a contrast image and a tissue image based on the reflection waves of the ultrasonic waves transmitted by the ultrasound probe 3. The ultrasound diagnosis apparatus 1 according to the first embodiment avoids the depolarization of the piezoelectric vibrator 354, by use of the connector 32 that is explained in detail below, so that the performance of the ultrasound probe 3 can be prevented from lowering. More specifically, the connector 32 according to the first embodiment avoids the depolarization by passing pyroelectric charges, which are the main factor of the depolarization of the piezoelectric vibrator 354, to the ground (GND). As a result, the ultrasound diagnosis apparatus 1 according to the first embodiment can prevent the performance of the ultrasound probe 3 from being degraded.

The structure of the connector 32 of the ultrasound diagnosis apparatus 1 according to the first embodiment is now explained with reference to FIG. 4. FIG. 4 is a diagram for explaining the structure of the connector 32 in the ultrasound diagnosis apparatus 1 according to the first embodiment. As illustrated in the top part of FIG. 4, the connector 32 of the ultrasound diagnosis apparatus 1 according to the first embodiment includes an open/short switching board 321, a short terminal 322, a core (iron core) 323, a solenoid 324, and actuator control lines 325.

The open/short switching board 321 switches at any timing between a short state in which the electrode of the piezoelectric vibrator 354 is connected to the GND and an open state in which this electrode is not connected to the GND, by establishing contact with, or separating from, the later described short terminal 322. More specifically, as illustrated in the top part of FIG. 4, the open/short switching board 321 is a board through which all the signal lines 36 included in the cable 34 run, and it switches between the short state in which all the electrodes of the piezoelectric vibrator 354 are connected to the GND and the open state in which the electrodes are not connected to the GND, by establishing contact with or separating from the short terminal 322.

The short terminal 322 brings the electric circuit formed between the electrodes of the piezoelectric vibrator 354 into the short state or the open state by making contact with the open/short switching board 321 or separating from it. More specifically, as illustrated at the top of FIG. 4, the short terminal 322 brings the electric circuit formed between the electrodes of the piezoelectric vibrator 354 into the short state by making contact with the open/short switching board 321. Furthermore, as illustrated at the bottom of FIG. 4, the short terminal 322 brings the electric circuit formed between the electrodes of the piezoelectric vibrator 354 into the open state by separating from the open/short switching board 321.

Figure 5A:
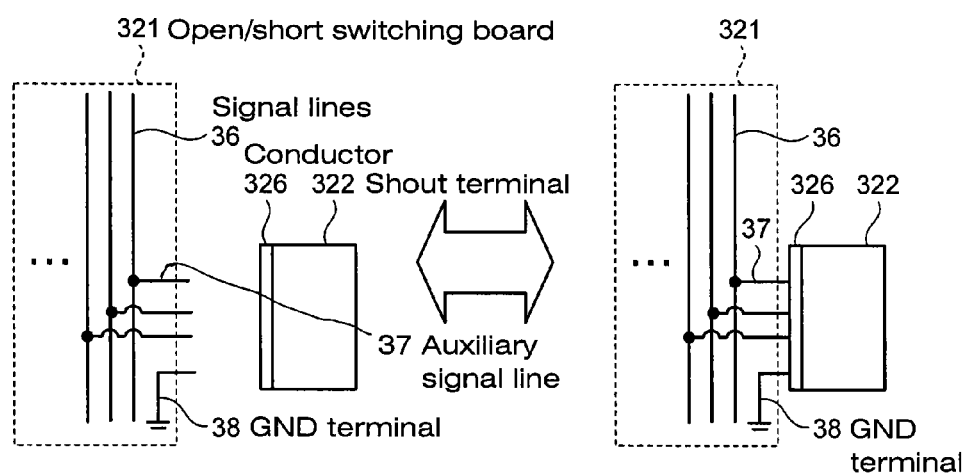
FIG. 5A is a diagram for explaining switching of a short state and an open state by an open/short switching board and a short terminal.
Figure 5B:
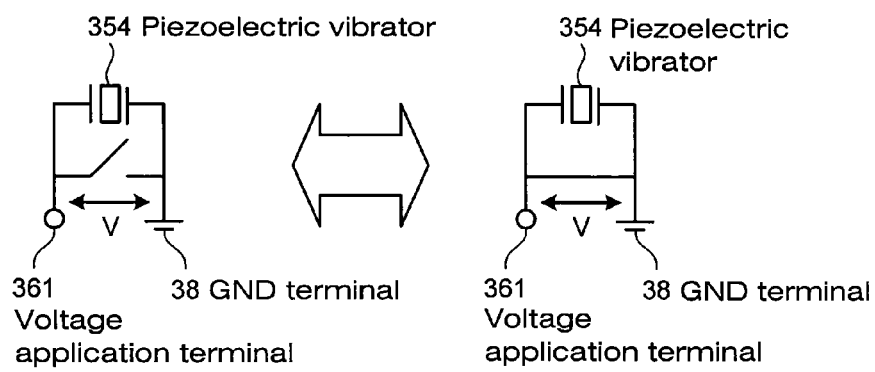
FIG. 5B is a diagram for explaining the state of an electric circuit in the short state and the open state.

Here, the switching operation between the short state and the open state by the open/short switching board 321 and the short terminal 322 is explained with reference to FIGS. 5A and 5B. FIG. 5A is a diagram for explaining the switching operation between the short state and the open state by the open/short switching board 321 and the short terminal 322. FIG. 5B is a diagram for explaining the electric circuit in the short state and the open state.

In FIG. 5A, the state of the signal lines where the open/short switching board 321 and the short terminal 322 are separated from each other is illustrated on the left side of FIG. 5A. Moreover, in FIG. 5A, the state of the signal lines where the open/short switching board 321 and the short terminal 322 are brought into contact with each other is illustrated on the right side of FIG. 5A. Moreover, regarding FIG. 5B, the state of the electric circuit where the open/short switching board 321 and the short terminal 322 are separated from each other as indicated on the left side of FIG. 5A is illustrated on the left side of FIG. 5B. Further, in FIG. 5B, the state of the electric circuit in which the open/short switching board 321 and the short terminal 322 are brought into contact with each other as indicated on the right side of FIG. 5A is illustrated on the right side of FIG. 5B.

As illustrated on the left side of FIG. 5A, the open/short switching board 321 includes the signal lines 36 that are connected to all the electrodes of the piezoelectric vibrator 354, and is provided with auxiliary signal lines 37 that extend externally from the signal lines toward the short terminal 322 and a GND terminal 38 one end of which extends externally toward the short terminal 322. In addition, as illustrated on the left side of FIG. 5A, the short terminal 322 includes a conductor 326 on the side of the open/short switching board 321.

Then, when the open/short switching board 321 and the short terminal 322 are brought into contact with each other, the protruding portions of all the auxiliary signal lines 37 are connected to the protruding portion of the GND terminal 38 by way of the conductor 326, as illustrated on the right side of FIG. 5A. The conductor 326 may be an electric circuit board or a conductive rubber.

In other words, when the open/short switching board 321 and the short terminal 322 are separated from each other, the electric circuit including the piezoelectric vibrator 354, a voltage application terminal 361, and the GND terminal 38 are brought into the open state, as illustrated on the left side of FIG. 5B. On the other hand, when the open/short switching board 321 and the short terminal 322 are in contact with each other, the electric circuit including the piezoelectric vibrator 354, the voltage application terminal 361, and the GND terminal 38 is brought into a short state, as illustrated on the right side of FIG. 5B.

For example, in accordance with a temperature change or the like, pyroelectric charges are generated in the piezoelectric vibrator 354. The pyroelectric charges generate a voltage in a direction opposite to the voltage direction of the piezoelectric polarization of the piezoelectric vibrator 354. Thus, if a significant amount of pyroelectric charges are generated, depolarization that weakens the piezoelectric polarization of the piezoelectric vibrator 354 is produced, which lowers the performance of the ultrasound probe 3.

The open/short switching board 321 and the short terminal 322, however, bring the electric circuit of the electrodes of the piezoelectric vibrator 354 into the short state illustrated on the right side of FIG. 5B so that the pyroelectric charges produced in the piezoelectric vibrator 354 can flow into the GND terminal 38. In other words, with the electric circuit of the electrodes of the piezoelectric vibrator 354 in the short state, even if a thermal load is applied onto the piezoelectric vibrator 354, no depolarization would occur, and the performance of the ultrasound probe 3 would be prevented from being degraded. In an ultrasound diagnosis with the ultrasound diagnosis apparatus 1, the electric circuit of the electrodes of the piezoelectric vibrator 354 is put into the open state as illustrated on the right side of FIG. 5B, and thereby a voltage necessary to drive the ultrasound probe 3 can be applied.

In FIG. 4, the iron core 323 is a fixed iron core of the solenoid actuator mechanism that moves the short terminal 322. The solenoid 324 is a three-dimensional coil of the solenoid actuator mechanism. The actuator control lines 325 pass the current supplied from the apparatus main body 2 to the solenoid 324.

The operation of moving the short terminal 322 with the solenoid actuator mechanism is explained now. The short terminal 322 moves toward the iron core 323 when the current supplied from the apparatus main body 2 flows into the solenoid 324 by way of the actuator control lines 325. More specifically, the short terminal 322 is arranged at a position a certain distance away from the iron core 323 (i.e. a position in contact with the open/short switching board 321) by use of a spring or the like. Then, when a current flows into the solenoid 324, the short terminal 322 moves until it is tightly attached to the iron core 323 by suction that acts between the solenoid 324 and the iron core 323, owing to the magnetic flux produced in the solenoid 324.

The short terminal 322 maintains the tight attachment with the iron core 323 during the supply of the current to the solenoid 324. Then, once a current supply to the solenoid 324 stops, the short terminal 322 returns to the original position (i.e., the position in contact with the open/short switching board 321) by the action of the spring or the like.

In other words, when no current is supplied to the solenoid 324, the short terminal 322 comes into contact with the open/short switching board 321, and brings the electric circuit formed between the electrodes of the piezoelectric vibrator 354 into a short state. Then, when a current is supplied into the solenoid 324, the short terminal 322 is separated from the open/short switching board 321, and brings the electric circuit formed between the electrodes of the piezoelectric vibrator 354 into an open state.

As mentioned above, the open/short switching board 321 and the short terminal 322 switch between the short state and the open state in accordance with the current supplied from the apparatus main body 2 by way of the actuator control lines 325. The timing of the current supplied from the apparatus main body 2 can be arbitrarily determined by the operator of the ultrasound diagnosis apparatus 1. In other words, the operator can arbitrarily switch the short state and the open state. In the following explanation, an example of the timing of switching from the short state to the open state and an example of the timing of switching from the open state to the short state are discussed with reference to FIGS. 6 and 7.

Figure 6:
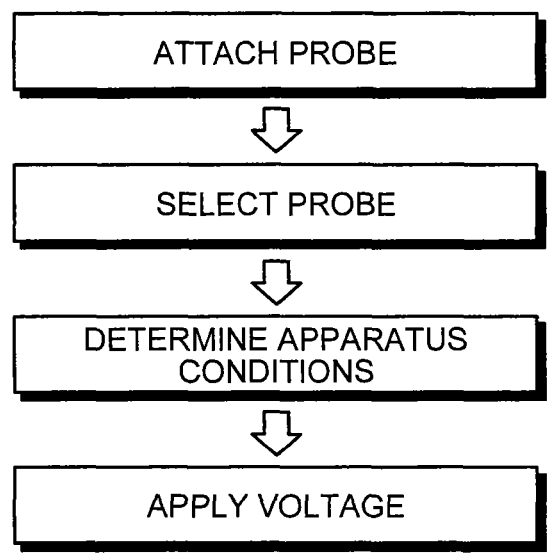
FIG. 6 is a diagram for explaining the timing of switching from the short state to the open state.

FIG. 6 is a diagram for explaining an example of the timing of switching from the short state to the open state. As indicated in FIG. 6, between the connection of the ultrasound probe 3 to the apparatus main body 2 and the initiation of an ultrasound diagnosis, there are several timings at which switching from the short state to the open state may be performed.

For example, before the ultrasound diagnosis is started, first, the ultrasound probe 3 is attached to the apparatus main body 2. At this point, the ultrasound probe 3 is physically connected the apparatus main body 2 and is in a short state.

Then, when the ultrasound probe 3 is selected as a probe that is to be used for the ultrasound diagnosis (for example, when it is selected as a probe that is to be used for the ultrasound diagnosis from multiple ultrasound probes), the current is allowed to pass from the apparatus main body 2 to the ultrasound probe 3. Thus, the apparatus main body 2 can supply a current to the solenoid 324 by way of the actuator control lines 325. In other words, the operator can switch it from the short state to the open state at this timing.

If the switching to the open state is not performed here, the next possible timing of switching from the short state to the open state can be when the apparatus conditions are determined, as indicated in FIG. 6. In other words, the operator can perform switching from the short state to the open state at the same time as when various settings and the like for the ultrasound diagnosis are input.

Furthermore, if the switching to the open state is not performed at the timing of determining the apparatus conditions, the open state should be established at the timing of applying a voltage to the ultrasound probe 3, as illustrated in FIG. 6, and the switching may be performed immediately before the voltage application (i.e., immediately before releasing the freeze button). To avoid the depolarization of the piezoelectric vibrator 354 as much as possible, it is the most effective to perform the switching to the open state immediately before the voltage application.

Figure 7:
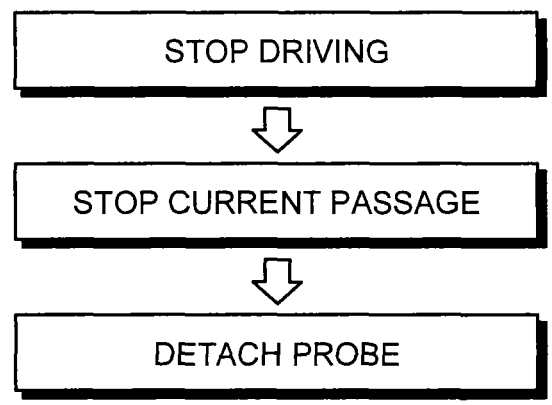
FIG. 7 is a diagram for explaining the timing of switching from the open state to the short state.

FIG. 7 is a diagram for explaining an example of the timing of switching from the open state to the short state. As indicated in FIG. 7, between the termination of the ultrasound diagnosis and the detachment of the ultrasound probe 3 from the apparatus main body 2, there are several timings at which the switching from the open state to the short state can be conducted.

For example, as indicated in FIG. 7, the switching from the open state to the short state may be performed at the timing when the drive of the ultrasound probe 3 is stopped (i.e., when the voltage application is stopped). If the switching to the short state is not performed here, the next possible timing of switching from the open state to the short state is when the current from the apparatus main body 2 to the ultrasound probe 3 is stopped, as indicated in FIG. 7.

When the current from the apparatus main body 2 to the ultrasound probe 3 is stopped, the current supplied from the apparatus main body 2 to the solenoid 324 is also automatically stopped. Thus, by the time the ultrasound probe 3 is detached, the electric circuit of the electrodes of the piezoelectric vibrator 354 is brought into the short state, as indicated in FIG. 7.

As discussed above, the switching between the short state and the open state can be conducted at any timing by the operator. The disclosed technology, however, is not limited to the above, and for example, it may be configured in such a manner that the switching is automatically performed in accordance with the conductivity between the apparatus main body 2 and the ultrasound probe 3.

As described above, according to the first embodiment, the open/short switching board 321 and the short terminal 322 switch at any timing between the short state in which the electrodes of the piezoelectric vibrator 354 in the ultrasound probe 3 are connected to the GND terminal 38 and the open state in which the electrodes of the piezoelectric vibrator 354 are not connected to the GND terminal 38. Thus, the ultrasound diagnosis apparatus 1 according to the first embodiment drains the pyroelectric charge, which is the main factor that causes the depolarization of the piezoelectric vibrator 354, to the ground (GND) to avoid the depolarization. As a result, the ultrasound diagnosis apparatus 1 according to the first embodiment can prevent the performance of the ultrasound probe 3 from being degraded.

For example, in the conventional technologies, an electric circuit has been known that dissipates pyroelectric charges produced in the piezoelectric vibrator to a resistor that is added to the electric circuit of the electrodes of the piezoelectric vibrator. FIG. 8 is a diagram for explaining an example of a conventional technology having an electric circuit of the electrodes of the piezoelectric vibrator. In the conventional electric circuit, a parallel resistance component 362 is added, as illustrated in FIG. 8, to the electric circuit having the voltage application terminal 361, the piezoelectric vibrator 354, and the GND terminal 38. In this manner, in the conventional electric circuit, pyroelectric charges generated in the piezoelectric vibrator 354 can be dissipated to the parallel resistance component 362.

The conventional method may suppress the depolarization to some extent if the pyroelectric charges are generated due to a temperature change or the like, but if a significant amount of pyroelectric charges are generated, the depolarization cannot be suppressed, which results in degradation in the performance of the ultrasound probe 3.

In the ultrasound diagnosis apparatus 1 according to the first embodiment, because the pyroelectric charges generated in the piezoelectric vibrator 354 are drained to the GND terminal 38, depolarization does not occur in the piezoelectric vibrator 354 even if a significant amount of pyroelectric charges are generated. Thus, by use of the disclosed technology, a highly reliable ultrasound probe tolerant of a thermal load can be offered.

In addition, the apparatus main body 2 according to the first embodiment electrically controls the operation of switching between the short state and the open state performed by the open/short switching board 321 and the short terminal 322, based on the condition of the connection between the apparatus main body 2 and the ultrasound probe 3. Hence, the ultrasound diagnosis apparatus 1 according to the first embodiment can be readily realized.

Moreover, according to the first embodiment, the apparatus main body 2 switches between the short state and the open state by a solenoid actuator mechanism that uses electromagnetic force. Hence, the ultrasound diagnosis apparatus 1 according to the first embodiment can realize an accurately operating switching mechanism, with a simple structure.

[Second Embodiment]

According to the first embodiment, the control of the contact between the open/short switching board 321 and the short terminal 322 and separation thereof by use of a solenoid actuator mechanism that uses a current supplied from the apparatus main body 2 has been explained. According to the second embodiment, the control of the contact between the open/short switching board 321 and the short terminal 322 and separation thereof by interlocking the short terminal 322 and the connecting mechanism 33 is explained below.

FIG. 9 is a diagram for explaining the structure of the connector 32 in the ultrasound diagnosis apparatus 1 according to the second embodiment. As illustrated at the top of FIG. 9, in the connector 32 of the ultrasound diagnosis apparatus 1 according to the second embodiment, the short terminal 322 is mechanically connected to the connecting mechanism 33. More specifically, the short terminal 322 is connected to the connecting mechanism 33 in such a manner that its position changes in accordance with the movement of the connecting mechanism 33.

For example, as illustrated at the top of FIG. 9, when the connecting mechanism 33 is unlocked, the short terminal 322 is connected to the connecting mechanism 33 in such a manner that it is brought into contact with the open/short switching board 321. Furthermore, when the connecting mechanism 33 is pushed toward the not-shown apparatus main body 2 and locked, the short terminal 322 is connected to the connecting mechanism 33 in such a manner that it is separated from the open/short switching board 321, as illustrated at the bottom of FIG. 9.

In other words, when the ultrasound probe 3 is connected and fixed to the apparatus main body 2, the connector 32 of the ultrasound diagnosis apparatus 1 according to the second embodiment is in the open state, and when the fixation is cancelled, it is brought into the short state. For example, if the connecting mechanism 33 is a handle, the short terminal 322 is brought into contact with the open/short switching board 321 or is separated from it, in accordance with the rotation of the handle that switches between the locked state and the unlocked state. The connecting mechanism 33 may also be a knob or a switch, and the short terminal 322 can be connected to the connecting mechanism 33 in such a manner as to interlock with it.

As described above, according to the second embodiment, the open/short switching board 321 and the short terminal 322 switch between the short state and the open state based on a change of the arrangement position in accordance with the connection state of the apparatus and the ultrasound probe. Thus, the ultrasound diagnosis apparatus 1 according to the second embodiment can further readily switch between the short state and the open state.

In addition, according to the second embodiment, the open/short switching board 321 and the short terminal 322 are interlocked with the mechanism that connects the apparatus to the ultrasound probe to switch between the short state and the open state. Hence, the ultrasound diagnosis apparatus 1 according to the second embodiment can reliably switch between the short state and the open state at the timings of starting and terminating the ultrasound diagnosis.

[Third Embodiment]

Explanations have been provided regarding the first and second embodiments. However, various modifications can be made in addition to the first and second embodiments.

(1) Modification Example 1

According to the second embodiment, the operation of switching between the short state and the open state by interlocking the short terminal 322 with the connecting mechanism 33. The disclosed technology is not limited thereto, however. For example, the operation of switching between the short state and the open state may be realized by changing the position of the short terminal 322 by a mechanism included in the apparatus main body 2.

Figure 10:
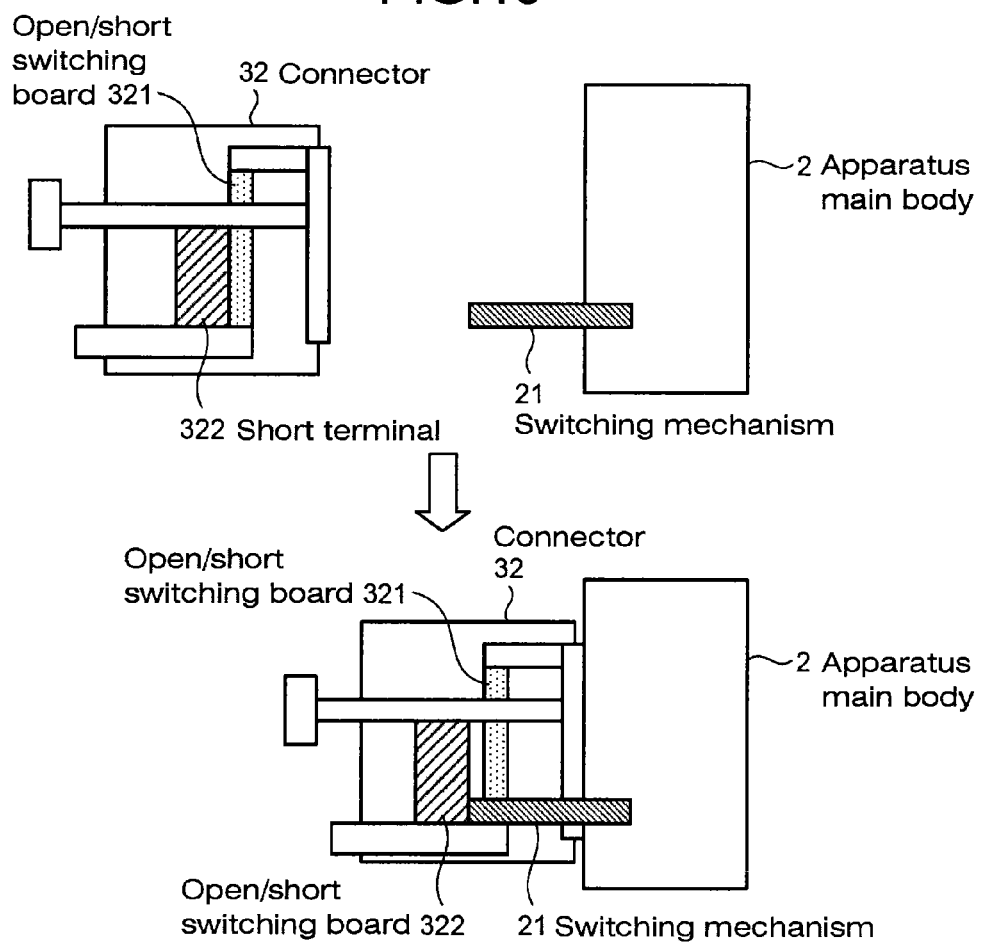
FIG. 10 is a diagram for explaining the structure of a connector of an ultrasound diagnosis apparatus according to the third embodiment.

FIG. 10 is a diagram for explaining the structure of the connector 32 of the ultrasound diagnosis apparatus 1 according to the third embodiment. As illustrated at the top of FIG. 10, the apparatus main body 2 of the ultrasound diagnosis apparatus 1 according to the third embodiment is provided with a switching mechanism 21. Then, in the connector 32 of the ultrasound diagnosis apparatus 1 according to the third embodiment, the short terminal 322 is mechanically connected to the connecting mechanism 33 by way of a spring or the like. Here, the short terminal 322 is arranged at a position in contact with the open/short switching board 321, as illustrated at the top of FIG. 10.

Then, as illustrated at the bottom of FIG. 10, when the connector 32 is connected to the apparatus main body 2, the switching mechanism 21 pushes the short terminal 322 off. As a result, the short terminal 322 is moved to a position apart from the open/short switching board 321. When the connector 32 is detached from the apparatus main body 2, it returns to the original position by the action of the spring or the like.

In other words, in the connector 32 of the ultrasound diagnosis apparatus 1 according to the third embodiment, the open state is established when the connector 32 is connected to the apparatus main body 2, while the short state is established when the connector 32 is detached from the apparatus main body 2. In such a situation, even if the connector 32 is not locked, the ultrasound probe 3 can still be brought into the open state.

(2) Electrical Movement Control of Short Terminal

In the explanation of the first embodiment, the short terminal 322 that is moved by use of the solenoid actuator mechanism has been dealt with. However, the disclosed technology is not limited thereto, and for example, the short terminal 322 may be moved by use of a switch circuit.

(3) Arrangement of Open/short Switching Board and Short Terminal

According to the first embodiment, the open/short switching board and the short terminal are included in the connector 32. The disclosed technology, however, is not limited thereto. For example, the open/short switching board and the short terminal may be included in the ultrasound transmitting and receiving unit 35.

In such a situation, for example, the structure of the ultrasound probe 3 should be changed in such a manner that the solenoid actuator mechanism is included in the ultrasound transmitting and receiving unit 35 and a current is supplied thereto from the apparatus main body 2 by way of the cable 34.

(4) Modification Example 2

In the explanation of the first and second embodiments, the operation of switching between the short state and the open state that is performed based on the connection state of the ultrasound probe 3 and the apparatus main body 2 has been dealt with. However, the embodiment is not limited thereto, and, for example, the ultrasound probe 3 may singly perform the operation of switching between the short state and the open state at any timing that the operator desires, regardless of the connection state between the ultrasound probe 3 and the apparatus main body 2. An example of the ultrasound probe 3 singly performing the operation of switching between the short state and the open state at any timing that the operator desires is explained below with reference to FIGS. 11A and 11B.

Figure 11A:
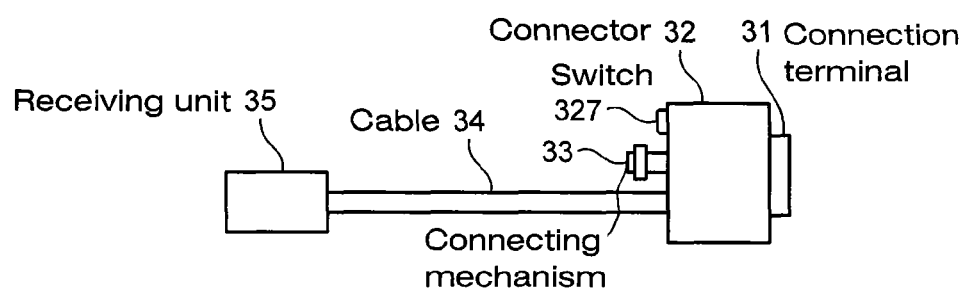
FIG. 11A is the first diagram for explaining a modified example of the third embodiment.
Figure 11B:
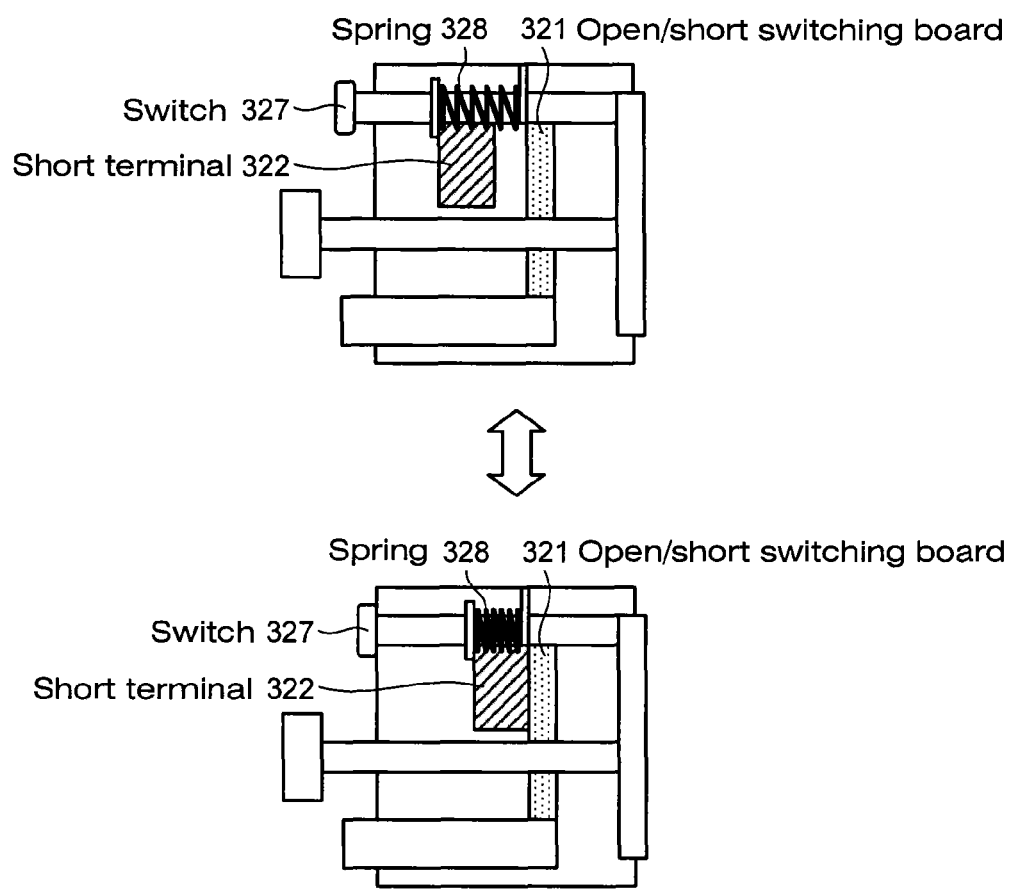
FIG. 11B is the second diagram for explaining a modified example of the third embodiment.

FIG. 11A is the first diagram of a modification example according to the third embodiment. Further, FIG. 11B is the second diagram of a modification example according to the third embodiment. For example, in the modification example according to the third embodiment, the ultrasound probe 3 includes a switch 327, as illustrated in FIG. 11A. Then, the operator presses the switch 327 down to switch between the short state and the open state at a timing that the operator desires.

As an example of the ultrasound probe 3 having the above switch 327, the short terminal 322 is mechanically connected to a support member that is interlocked with the switch, as illustrate at the top of FIG. 11B. Then, the ultrasound probe 3 switches between the short state and the open state by a spring 328 that stretches and contracts by the switch 327 that is pressed. For example, when the switch is pressed down in the situation illustrated at the top of FIG. 11B, the spring 328 contracts as illustrated at the bottom of FIG. 11B, which brings the short terminal 322 into contact with the open/short switching board 321 and establishes the short state. The switch 327 is provided with a holding member to hold the spring 328 in the contraction state.

Then, when the switch is pressed again in the situation illustrated at the bottom of FIG. 11B, the holding member is released, and the short terminal 322 and the open/short switching board 321 are separated from each other by the resilience of the spring 328, establishing the open state, as illustrated at the top of FIG. 11B. For the core of the spring 328, any material that can stretch and contract can be adopted.

In the explanation of the above examples, the switching between the short state and the open state is mechanically controlled, but the present embodiment is not limited thereto. For example, it may be electrically controlled. For example, a structure with a small battery in the connector may be adopted to perform electrical control.

As described above, the ultrasound probe according to the present embodiments can avoid the depolarization in the piezoelectric vibrators by switching between the short state and the open state of the piezoelectric vibrators. In addition to the above embodiments, a method of attaching a mass shorting board to the outside of the ultrasound probe may be considered for the switching between the open state and the short state of the piezoelectric vibrators.

However, with the method of attaching a mass shorting board to the outside of the ultrasound probe, two components, the ultrasound probe and the mass shorting board, are required for the structure. In other words, there is some inconvenience that the operator needs to handle the two components. Furthermore, with the method of using a mass shorting board, the operator may forget to attach it, or may not properly attach it, and thus it is difficult to reliably stop the generation of depolarization in the piezoelectric vibrators.

In contrast, the ultrasound probe according to the present embodiment includes a switching unit that switches between the short state and the open state, and therefore it is free of the above inconvenience or attaching error. In other words, in the ultrasound probe according to the present embodiment, the depolarization in the piezoelectric vibrators can be reliably avoided, without requiring the operator's awareness of the switching between the short state and the open state.

As explained above, according to the first, second, and third embodiments, the present ultrasound probe can avoid the depolarization in the piezoelectric vibrators, and can prevent the performance of the ultrasound probe from being degraded.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound probe comprising:
a plurality of piezoelectric vibrators configured to
generate ultrasound waves,
receive reflection waves, and
generate a reception signal based on the received reflection waves for generating an ultrasonic image;
a switching board; and
a connecting mechanism configured to switch via an actuating mechanism between a short state in which an electrode of the plurality of piezoelectric vibrators is connected to a ground (GND) terminal on the switching board and an open state in which the electrode of the plurality of piezoelectric vibrators is not connected to the GND terminal on the switching board,
wherein the connecting mechanism switches all of the plurality of piezoelectric vibrators to the open state at a timing when the connection between the ultrasound probe and an apparatus main body that generates the ultrasonic image based on the reception signal is in a locked state, and switches all of the plurality of piezoelectric vibrators to the short state at a timing when the connection between the ultrasound probe and the apparatus main body is in an unlocked state.

2. The ultrasound probe according to claim 1, wherein the connecting mechanism is configured to switch between the short state and the open state by electrical control, based on a condition of connection between the ultrasound probe and the apparatus main body.

3. The ultrasound probe according to claim 1, wherein the connecting mechanism is configured to switch between the short state and the open state in accordance with a change of an arrangement position, based on a condition of connection between the ultrasound probe and the apparatus main body.

4. The ultrasound probe according to claim 2, wherein the connecting mechanism is configured to switch between the short state and the open state by an actuator that uses an electromagnetic force.

5. The ultrasound probe according to claim 3, wherein the switching board is interlocked with a handle or a knob or a switch for connecting the ultrasound probe to the apparatus main body and switches between the short state and the open state.

6. The ultrasound probe according to claim 1, wherein the connecting mechanism is configured to switch between the short state and the open state at a timing of accepting an input operation from an operator.

7. The ultrasound probe according to claim 1, wherein the connecting mechanism is configured to switch between the short state and the open state at a predetermined timing.

8. An ultrasound diagnosis apparatus comprising:
an ultrasound probe; and
an apparatus main body that generates an ultrasonic image based on a reception signal generated by the ultrasound probe,
wherein the ultrasound probe includes
plurality of piezoelectric vibrators configured to
generate ultrasonic waves,
receive reflection waves, and
generate the reception signal based on the received reflection waves for generating the ultrasonic image, and
a switching board; and
a connecting mechanism configured to switch via an actuating mechanism between a short state in which an electrode of the plurality of piezoelectric vibrators is connected to a ground (GND) terminal on the switching board and an open state in which the electrode of the plurality of piezoelectric vibrators is not connected to the GND terminal on the switching board,
wherein the connecting mechanism switches all of the plurality of piezoelectric vibrators to the open state at a timing when the connection between the ultrasound probe and an apparatus main body that generates the ultrasonic image based on the reception signal is in a locked state, and switches all of the plurality of piezoelectric vibrators to the short state at a timing when the connection between the ultrasound probe and the apparatus main body is in an unlocked state.

* * * * *